United States Patent
Gardein

(10) Patent No.: US 11,617,852 B2
(45) Date of Patent: Apr. 4, 2023

(54) EMERGENCY EXHALATION VALVE COMPRISING DIAPHRAGM RING

(71) Applicant: Loewenstein Medical Technology S.A., Luxembourg (LU)

(72) Inventor: Joachim Gardein, Icod de los Vinos (ES)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 1206 days.

(21) Appl. No.: 15/619,654

(22) Filed: Jun. 12, 2017

(65) Prior Publication Data

US 2017/0354794 A1 Dec. 14, 2017

(30) Foreign Application Priority Data

Jun. 14, 2016 (DE) .......................... 102016007202.4

(51) Int. Cl.
*A61M 16/20* (2006.01)
*A61M 16/08* (2006.01)
*A61M 39/24* (2006.01)

(52) U.S. Cl.
CPC ...... *A61M 16/209* (2014.02); *A61M 16/0816* (2013.01); *A61M 16/0825* (2014.02); *A61M 2039/244* (2013.01)

(58) Field of Classification Search
CPC .. A61M 16/20; A61M 16/201; A61M 16/202; A61M 16/203; A61M 16/204; A61M 16/205; A61M 16/206; A61M 16/208; A61M 16/209; A61M 16/0825; A61M 16/0816; A61M 2039/2433; A61M 2039/244; A61M 2039/2446; A61M 2039/2453; A61M 2039/246
See application file for complete search history.

(56) References Cited

U.S. PATENT DOCUMENTS

| | | |
|---|---|---|
| 2004/0094157 A1 | 5/2004 | Dantanarayana et al. |
| 2004/0255948 A1 | 12/2004 | Smith et al. |
| 2009/0065729 A1 | 3/2009 | Worboys et al. |
| 2009/0272380 A1 | 11/2009 | Jaffre et al. |
| 2010/0258133 A1 | 10/2010 | Todd et al. |

(Continued)

FOREIGN PATENT DOCUMENTS

| | | |
|---|---|---|
| DE | 202011107053 U1 | 11/2011 |
| EP | 2845618 A1 | 3/2015 |

(Continued)

OTHER PUBLICATIONS

American Heritage Dictionary, Definition of "hinge", https://www.ahdictionary.com/word/search.html?q=hinge, accessed Oct. 5, 2020 (Year: 2020).*

*Primary Examiner* — Elliot S Ruddie
(74) *Attorney, Agent, or Firm* — Abel Schillinger, LLP

(57) ABSTRACT

Disclosed is a connecting piece for artificial respiration. The connecting piece comprises an opening that faces a ventilation hose, an opening disposed toward a patient interface, and an opening to the atmosphere which can be at least partially closed from the inside by a diaphragm. The connecting piece further has a diaphragm opening for accommodating the diaphragm into the connecting piece, the diaphragm being held via a diaphragm ring that surrounds the connecting piece.

19 Claims, 5 Drawing Sheets

(56) References Cited

U.S. PATENT DOCUMENTS

| | | | | |
|---|---|---|---|---|
| 2013/0306066 A1* | 11/2013 | Selvarajan | ............ | A61M 16/06 |
| | | | | 128/202.27 |
| 2014/0150798 A1* | 6/2014 | Fong | ................ | A61M 16/0622 |
| | | | | 128/206.21 |
| 2015/0059763 A1* | 3/2015 | Chien | ............... | A61M 16/0683 |
| | | | | 128/206.26 |
| 2015/0136137 A1 | 5/2015 | Bugamelli et al. | | |
| 2016/0015918 A1* | 1/2016 | Kuriger | ............ | A61M 16/0069 |
| | | | | 128/204.23 |

FOREIGN PATENT DOCUMENTS

| | | | | | |
|---|---|---|---|---|---|
| EP | 3254721 | A1 * | 12/2017 | ........ | A61M 16/0616 |
| WO | 02051486 | A1 | 7/2002 | | |
| WO | 2007045008 | A1 | 4/2007 | | |
| WO | 2013006899 | A1 | 1/2013 | | |
| WO | 2013171705 | A1 | 11/2013 | | |
| WO | WO-2016124145 | A1 * | 8/2016 | ........ | A61M 16/0816 |

* cited by examiner

EMERGENCY EXHALATION VALVE COMPRISING DIAPHRAGM RING

CROSS-REFERENCE TO RELATED APPLICATIONS

The present application claims priority under 35 U.S.C. § 119 of German Patent Application No. 10 2016 007 202.4, filed Jun. 14, 2016, the entire disclosure of which is expressly incorporated by reference herein.

BACKGROUND OF THE INVENTION

1. Field of the Invention

The present invention relates to a ventilator which comprises an integrated emergency exhalation valve and is designed as a patient interface. Ventilators are significant for patients who suffer from a disruption of the supply of breathable air or oxygen, wherein respiratory gas or oxygen-enriched air is supplied to the patient with positive pressure support via a patient interface which is often designed as a full face mask.

2. Discussion of Background Information

Emergency exhalation valves (AAV—anti-asphyxia valves) are known. They are used, in the event that respiration is interrupted, for example, due to a malfunction or failure of the therapy device, for enabling the patient to breathe in air from the room via an opening to the atmosphere and to give off the $CO_2$-enriched exhaled air into the surroundings.

The anti-asphyxia valves known from the prior art do not meet all the requirements on safety and hygiene or they are expensive and/or complicated to manufacture.

SUMMARY OF THE INVENTION

The present invention provides a connecting piece for artificial respiration, having an opening that faces the ventilation hose, an opening disposed toward the patient interface, and an opening to the atmosphere, which can be at least partially closed from the inside by means of a diaphragm, wherein the connecting piece has a diaphragm opening for accommodating the diaphragm into the connecting piece, and the diaphragm is held via a diaphragm ring which surrounds the connecting piece.

In one aspect thereof, the connecting piece may comprise a groove for the diaphragm ring in at least sections of the outer circumference of the connecting piece.

In another aspect, a guide segment on the diaphragm ring and a corresponding guide receptacle in the connecting piece may establish the installation position of the diaphragm ring and the diaphragm.

In yet another aspect, the diaphragm displacement in the connecting piece may be delimited by at least one stop and at least one ridge, and the stop and the ridge may each form a contact surface for the diaphragm.

In a still further aspect, the connecting piece may comprise connecting elements for connection to a rotating sleeve.

In another aspect, the connecting piece may have an outer diameter, at least in sections, which corresponds to the outer diameter of the rotating sleeve, at least in sections.

In another aspect, the connecting piece may have an outer diameter, at least in sections, which corresponds to the outer diameter of the diaphragm ring.

In another aspect, the connecting piece may have an outer diameter, at least in the area of the diaphragm opening, which is greater than the inner diameter of the diaphragm ring.

In another aspect, the width of the ring may be greater, at least in sections, than the width of the groove.

In another aspect, the diaphragm opening may be designed to taper conically inward.

In another aspect, the diaphragm may be connected to the diaphragm ring via a hinge.

In another aspect, a sealing area may also disposed between the hinge and the ring, which is used for closing the diaphragm opening in the connecting piece.

In another aspect, the diaphragm ring may be produced as one piece with the diaphragm from silicone or another elastomer.

In another aspect, the diaphragm may have a thickness of from about 0.4 mm to about 1.0 mm and the hinge may be thinner than the diaphragm.

In another aspect, a gap may remain between the diaphragm and the inner diameter of the ring, in order to allow the diaphragm to swing freely.

BRIEF DESCRIPTION OF THE DRAWINGS

The following Figures illustrate embodiments of the emergency exhalation valve.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
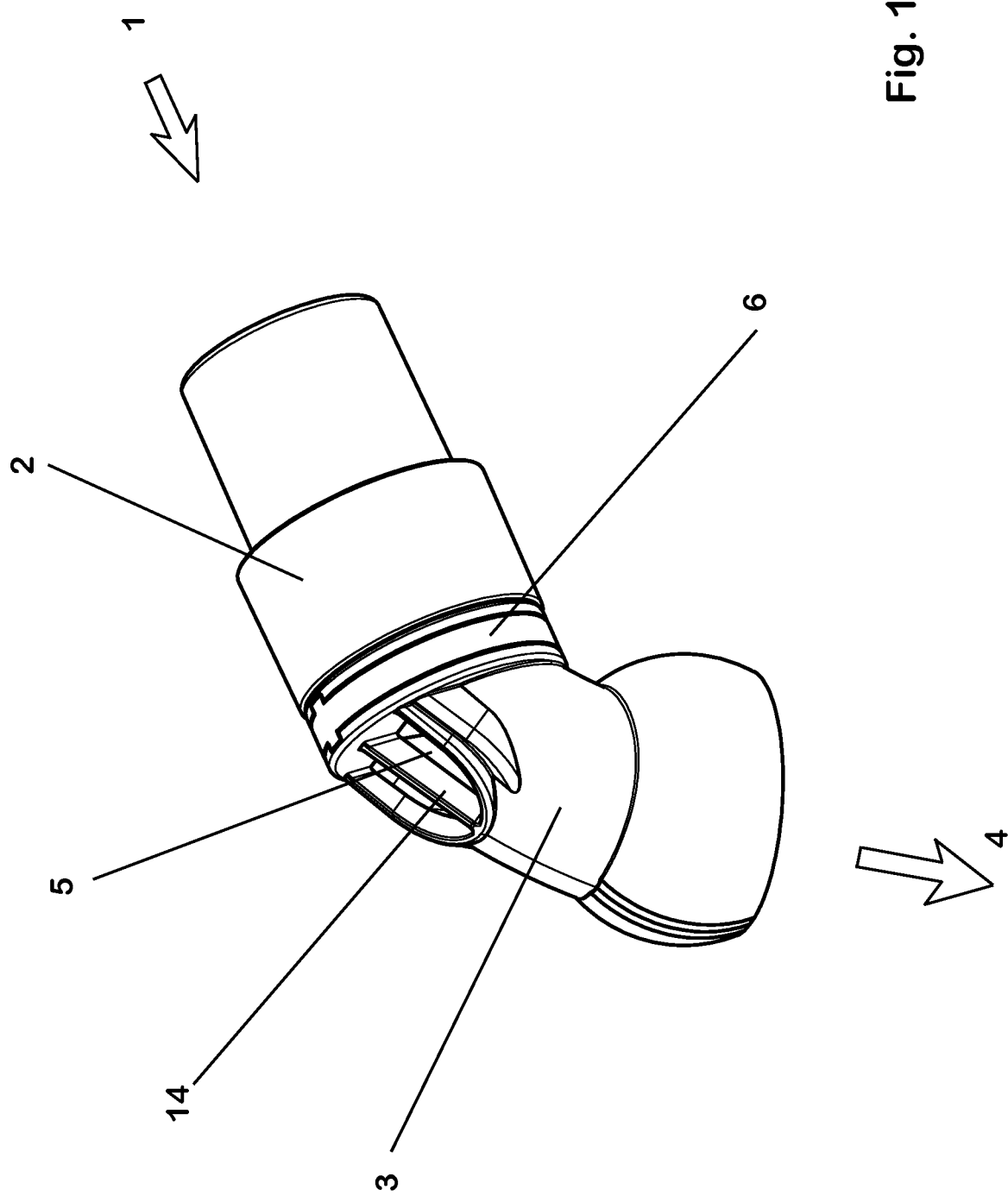
FIG. 1 shows a connecting piece having an opening to the atmosphere and a rotating sleeve.

FIG. 1 shows a connecting piece (3) for artificial respiration, having an opening that faces the ventilation hose (1), an opening disposed toward the patient interface (4), and an opening to the atmosphere (5) which can be at least partially closed from the inside by means of a diaphragm (7), wherein the connecting piece (3) has a diaphragm opening (13) for accommodating the diaphragm (7) into the connecting piece, and the diaphragm (7) is held via a diaphragm ring (6) which surrounds the connecting piece (3).

The therapy device is connected to the patient interface (4), for example, a ventilation mask, via a ventilation hose (1), a rotating sleeve (2), and a connecting piece (3) which is designed, for example, as an elbow coupling comprising a ball joint, and is used for supplying respiratory gas to the patient. The connecting piece (3) is disposed between the hose (1) and the patient interface (4) and conducts air. An opening to the atmosphere (5) is disposed in the connecting piece (3) in order to allow an unobstructed supply and discharge of air during interruptions in therapy. A diaphragm ring (6) is inserted into the flow channel (11) (shown here as an arrow) in such a way that the diaphragm (7) closes the opening to the atmosphere (5) during normal therapeutic operation by means of the pressure that is present. The therapeutic operation deflects the diaphragm out of its starting position. In the event of a pressure drop, the diaphragm folds back into its starting position. As a result, the diaphragm closes, at least partially, in the direction toward the hose (1) and thereby prevents rebreathing into the ventilation hose (1). The patient can now breathe ambient air via the opening to the atmosphere (5). FIG. 1 perspectively shows the design of the connecting piece having the opening to the atmosphere and comprising the inserted diaphragm ring (6) and a rotating sleeve, but without the hose and the ventilation mask.

Figure 2:
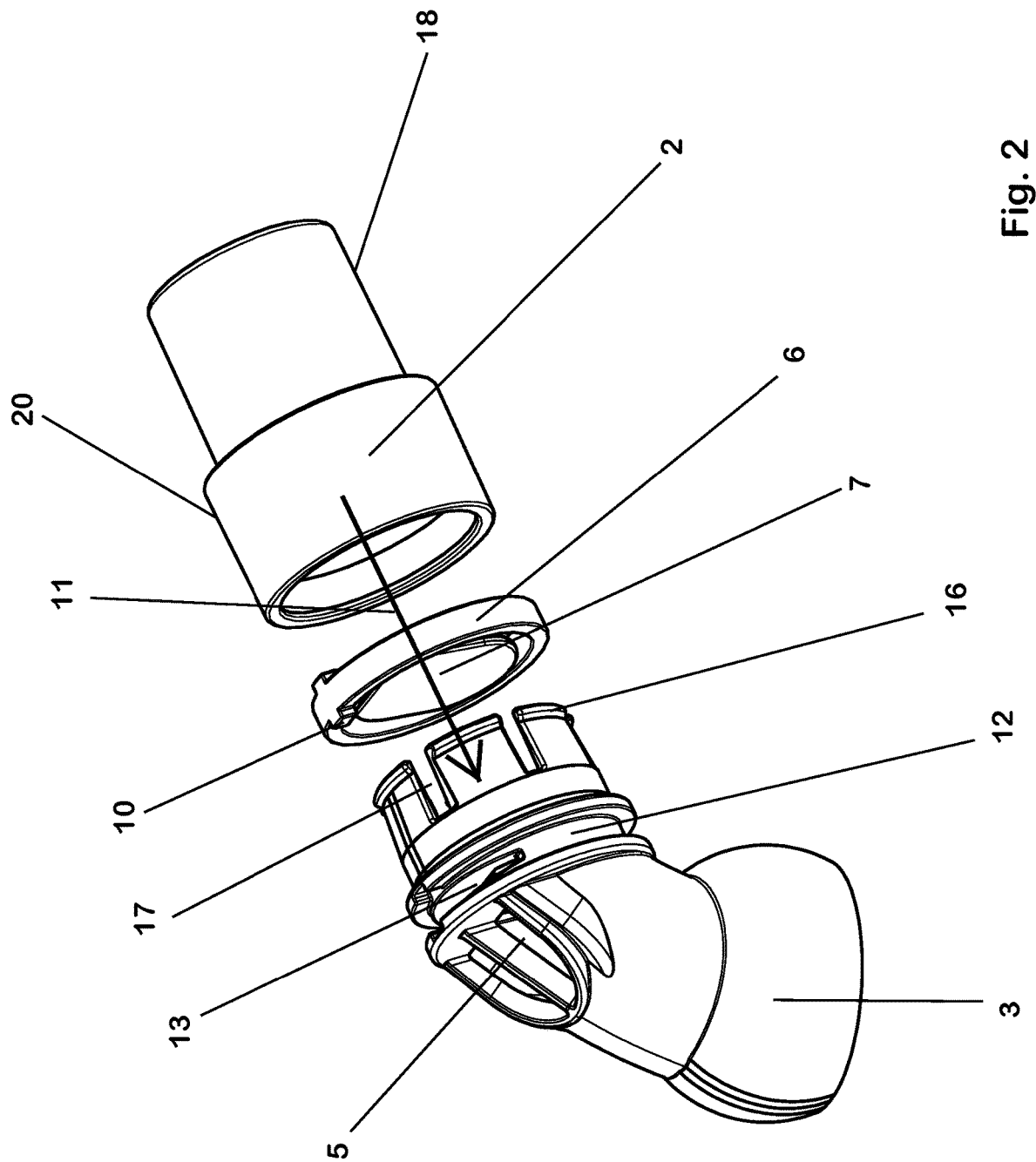
FIG. 2 is an exploded drawing comprising a diaphragm ring.
Figure 3:
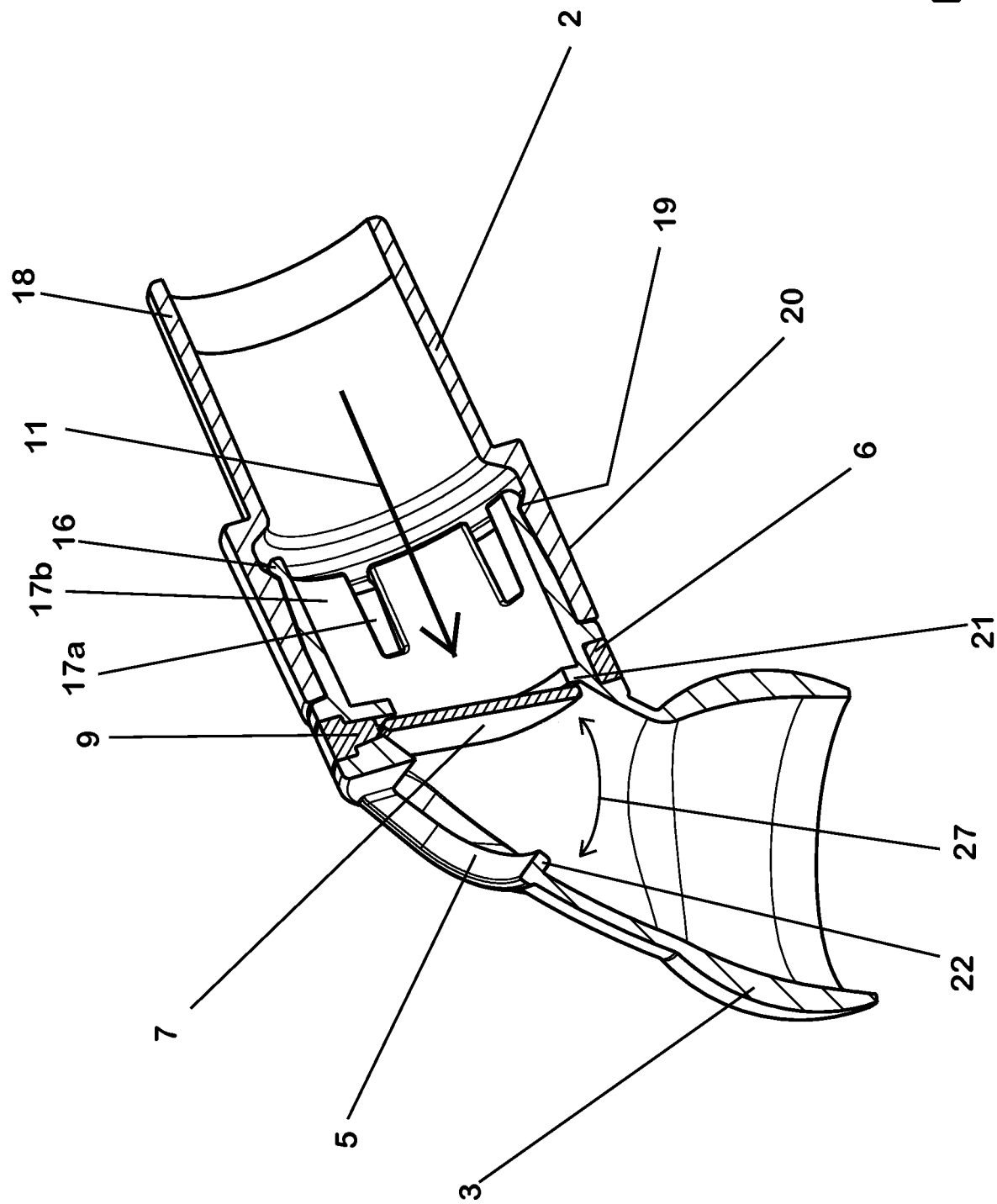
FIG. 3 shows a sectional representation comprising an inserted ring diaphragm.

FIG. 2 shows the same design in an exploded representation and, in FIG. 3, in a sectional representation.

The connecting piece (3), as shown in FIG. 2, has a diaphragm opening (13) and, for example, a groove (12) in the outer circumference. The groove (12) can be situated either peripherally or only in subareas on the circumference of the connecting piece (3) and is used for accommodating and fixing the diaphragm ring (6). The diaphragm ring is produced, for example, as one piece from silicone or another elastomer. The diaphragm (7), which is located on the diaphragm ring (6), is inserted through the diaphragm opening (13) into the flow channel (11) into the interior of the connecting piece (3). The ring (6a) of the diaphragm ring (6) is drawn over the hose connection side until it can be fixed in the groove (12). The rotating sleeve (2) is removed for this purpose. A guide segment (10) on the diaphragm ring (6) and the corresponding guide receptacle (28) in the connecting piece (3) are used as anti-rotation means and ensure that the diaphragm (7) is installed in the correct position.

The sectional representation in FIG. 3 shows the position of the diaphragm during a disruption in therapy. The diaphragm (7) of the emergency exhalation valve closes the flow channel and therefore exposes the opening to the atmosphere (5).

The diaphragm displacement (27) is indicated here using the curved arrow and is delimited, for example, by one stop (21, 22) and one segment (14, 15) in each direction. The stop and the segment (22 and 14) and (21 and 15) each form a planar contact surface against which the diaphragm can rest, depending on the situation (therapeutic operation or interruption in therapy).

Figure 4:
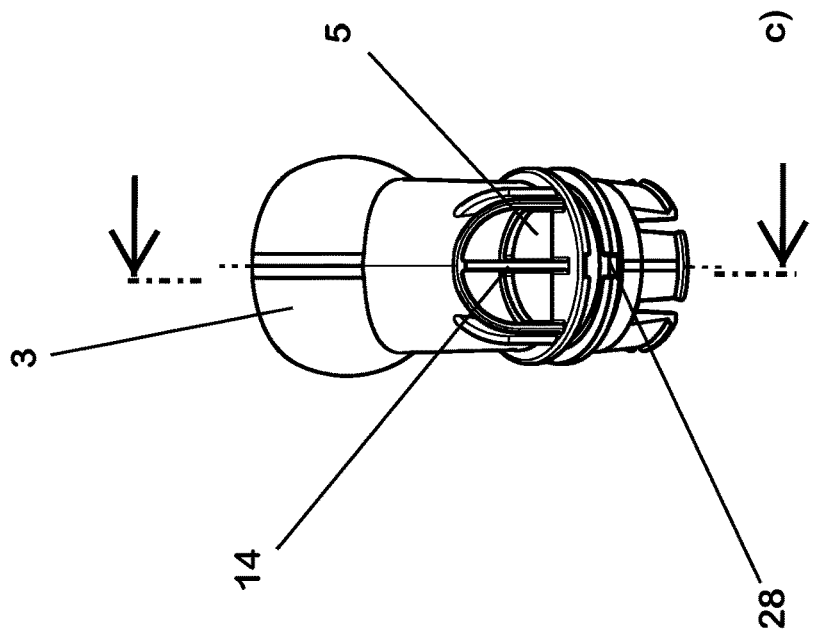
FIG. 4 shows various views a) to c) of the connecting piece.
Figure 4:
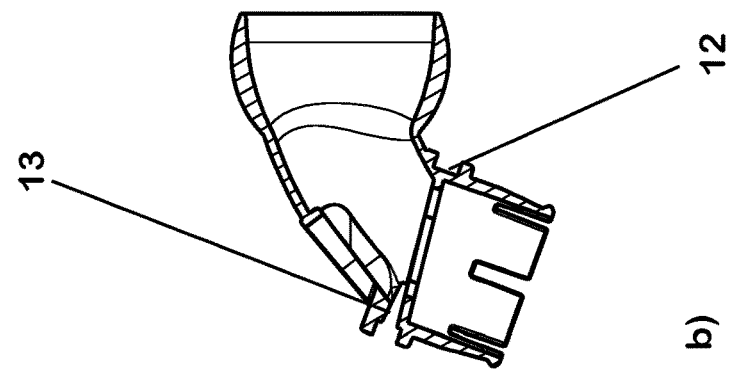
Figure 4:
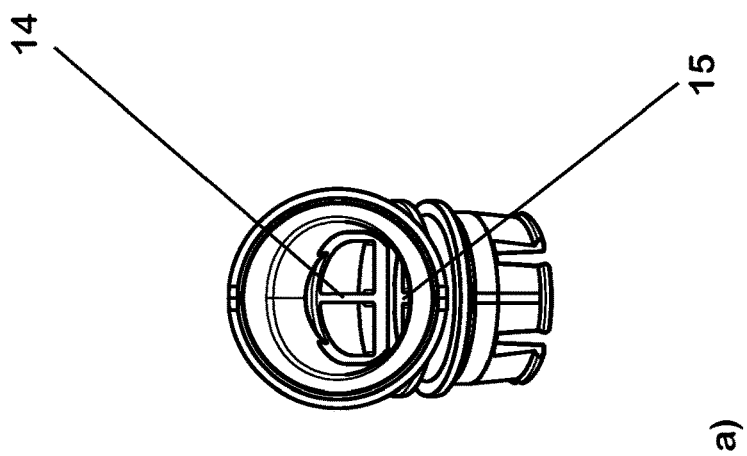

In the lateral sectional representation shown in FIG. 3 and FIG. 4, the segments (14 and 15) are partially hidden, since the course of the cut extends outside of the central axis, directly behind the segments, since the visible material of the segments would cover the openings otherwise.

The stop (21) is situated directly in the flow channel (11) of the connecting piece (3), as is also the case for the segment (15), and delimits the diaphragm displacement (27) when there is an interruption in therapy and no air flows in the direction toward the patient. The patient then breathes through the connecting piece and the respiratory gas presses the diaphragm against the stop (21) and the segment (15), which therefore partially close the airway in the direction of the hose. The stop (22), which is disposed, together with the segment (14), at the opening to the atmosphere (5), delimits the diaphragm displacement (27) in such a way that the diaphragm (7) can close the opening to the atmosphere (5) during therapeutic operation.

The rotating sleeve (2) comprising a hose cone (18), having a first outer diameter, onto which the ventilation hose can be slid. The rotating sleeve (2) has a second outer diameter in the area of the operating surface (20). The second outer diameter is greater than the first outer diameter. The second outer diameter is preferably selected to be identical to the outer diameter of the connecting piece, in the area of the contact surface of the rotating sleeve (2). The rotating sleeve (2) comprises connecting elements (19, undercut) on the inner side, in the section of the second outer diameter, for connection to the connecting piece. On the inner side, the rotating sleeve forms a circumferential undercut (19) which represents, for example, a rounded transition of the inner diameter from a smaller inner diameter to a larger inner diameter. The connecting piece forms corresponding connecting elements (16, 17) on its section facing the rotating sleeve (2). The connecting piece has recesses (17a) here, which expose spring tabs (17b). The spring tabs (17b) comprise, on their ends, slight bulges (16, chamfered edges) which snap into the undercut (19).

The position of the segments (14 and 15) in the connecting piece is apparent in FIG. 4 a).

FIG. 4 b) shows a cross-section of the connecting piece from the side. The groove (12) has a rectangular profile here, for example, and, above the opening (13), is wider than the opening. The opening (13) tapers conically.

The opening to the atmosphere (5) and the segment (14) lying therebelow are shown in FIG. 4 c). The guide receptacle (28) for the diaphragm ring is adjacent to the diaphragm opening (13).

Figure 5:
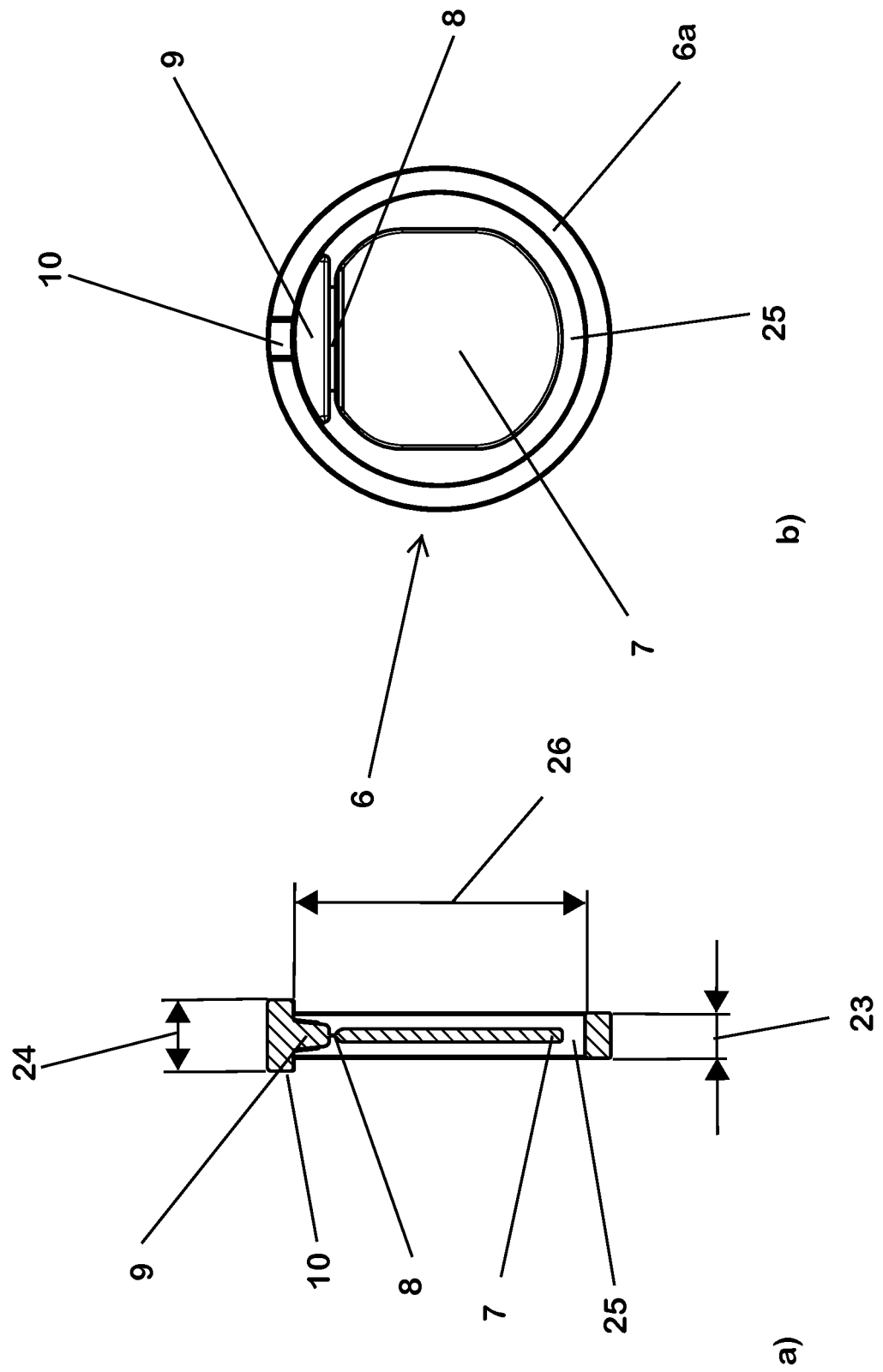
FIG. 5 shows two views a) and b) of the ring diaphragm.

FIG. 5 a) shows: The inner diameter (26) of the ring is designed to be smaller than the outer diameter of the connecting piece (3) in the area of the diaphragm opening (13), for example, in the area of the groove (12). As a result, it is achieved that the ring (6) is installed without play and centers itself by means of the expansion. The width (23, 24) of the ring (6a) is greater than the width of the groove (12), at least in sections. As a result, a circumferential seal of the ring (6a) with respect to the connecting piece (3) is ensured. The width (24) of the ring (6a) is greater than the width of the groove (12), in particular in the area that rests against the opening (13), in order to sealingly close the opening. The width (23) can be smaller than the width (24).

FIG. 5 b) shows: The diaphragm (7) is connected to the diaphragm ring (6) via a hinge (8), wherein a sealing area (9) is also disposed between the hinge (8) and the ring (6a). This sealing area (9) is used for closing the diaphragm opening (13) in the connecting piece (3). The sealing area (9) is designed to taper conically outward and is inserted into the diaphragm opening (13) in the connecting piece (3) so as to be flush therewith.

The diaphragm (7) may have a thickness of, for example, from about 0.5 mm to about 1.0 mm. The hinge (8) preferably may have a thickness of, for example, from about 0.2 mm to about 0.5 mm, but is always thinner than the diaphragm (7). The width of the hinge (7) may range, for example, from about 4.0 mm to about 10 mm and may have a length of, for example, from about 0.2 mm to about 1.0 mm.

FIG. 5 also shows that a gap (25) remains between the diaphragm and the inner diameter (26) of the ring, in order to allow the diaphragm to swing freely.

The material selected for the diaphragm ring (6) may be a silicone or a thermoplastic elastomer (TPE) having a Shore hardness ranging from about 30 to about 50 Shore A, for example, about 40 Shore A. The advantage of this inner emergency exhalation valve is that an additional outer component, which can get lost, is not required and there is no need for an additional outer seal, e.g., an insertion pocket or a diaphragm cartridge. The diaphragm may be designed as one piece with the diaphragm ring (6) and may be manufactured, for example, by injection molding.

While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

REFERENCE NUMBERS 1 ventilation hose (not shown)
2 rotating sleeve
3 connecting piece comprising ball joint
4 ventilation mask (not shown)
5 opening to the atmosphere
6 diaphragm ring
6*a* ring
7 diaphragm
8 hinge
9 sealing area
10 guide segment
11 flow channel
12 groove
13 diaphragm opening
14 segment for the outer diaphragm stop
15 segment for the inner diaphragm stop in the flow channel
16 chamfered edge
17*a* recess
17*b* spring tab
18 hose cone
19 undercut
20 operating surface
21 stop
22 stop
23 width 1
24 width 2
25 gap
26 inner diameter
27 diaphragm displacement
28 guide receptacle/anti-rotation means

What is claimed is:

1. A connecting piece for artificial respiration, wherein the connecting piece comprises an opening for facing a ventilation hose, an opening for connection to a patient interface, and an opening to the atmosphere which can be at least partially closed from an inside by a diaphragm, the connecting piece further comprising a diaphragm opening for accommodating the diaphragm in the connecting piece, and the diaphragm being held via a diaphragm ring which surrounds the connecting piece and being connected to the diaphragm ring via a hinge, the diaphragm opening being designed to taper conically inward.

2. The connecting piece of claim 1, wherein the connecting piece further comprises a groove for the diaphragm ring at least in sections of an outer circumference of the connecting piece.

3. The connecting piece of claim 1, wherein a guide segment on the diaphragm ring and a corresponding guide receptacle in the connecting piece establish an installation position of the diaphragm ring and the diaphragm.

4. The connecting piece of claim 1, wherein a diaphragm displacement in the connecting piece is delimited by at least one stop and at least one ridge, the stop and the ridge each forming a contact surface for the diaphragm.

5. The connecting piece of 1, wherein a sealing area for closing the diaphragm opening in the connecting piece is present between the hinge and the ring.

6. The connecting piece of claim 1, wherein the diaphragm ring is produced as one piece with the diaphragm.

7. The connecting piece of claim 1, wherein the diaphragm has a thickness of from 0.4 mm to 1 mm.

8. The connecting piece of claim 7, wherein the hinge is thinner than the diaphragm.

9. The connecting piece of claim 8, wherein the hinge has a thickness of from 0.2 mm to 0.5 mm.

10. The connecting piece of claim 9, wherein the hinge has a width of from 4.0 mm to 10 mm and a length of from 0.2 mm to 1.0 mm.

11. The connecting piece of claim 8, wherein the hinge has a width of from 4.0 mm to 10 mm.

12. The connecting piece of claim 8, wherein the hinge has a length of from 0.2 mm to 1.0 mm.

13. A patient interface, wherein the patient interface is connected to the connecting piece of claim 1.

14. The connecting piece of claim 1, wherein the diaphragm ring is made from a silicone.

15. The connecting piece of claim 1, wherein the diaphragm ring is made from a thermoplastic elastomer (TPE) having a Shore hardness ranging from 30 to 50 Shore A.

16. A connecting piece for artificial respiration, wherein the connecting piece comprises an opening for facing a ventilation hose, an opening for connection to a patient interface, and an opening to the atmosphere which can be at least partially closed from an inside by a diaphragm, the connecting piece further comprising a diaphragm opening for accommodating the diaphragm in the connecting piece, and the diaphragm being held via a diaphragm ring which surrounds the connecting piece and is produced as one piece with the diaphragm.

17. The connecting piece of claim 16, wherein the diaphragm ring is produced as one piece with the diaphragm from an elastomer.

18. The connecting piece of claim 17, wherein the elastomer comprises a silicone.

19. The connecting piece of claim 16, wherein a material for the diaphragm ring is selected from a silicone and a thermoplastic elastomer (TPE) having a Shore hardness ranging from 30 to 50 Shore A.

* * * * *